United States Patent
Chikkali et al.

(10) Patent No.: US 12,202,833 B2
(45) Date of Patent: Jan. 21, 2025

(54) HIGHLY EFFICIENT PROCESS FOR THE PREPARATION OF SITAGLIPTIN VIA RHODIUM CATALYZED ASYMMETRIC HYDROGENATION

(71) Applicant: Council of Scientific & Industrial Research, Delhi (IN)

(72) Inventors: Samir Hujur Chikkali, Pune (IN); Kishor Vilas Khopade, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 885 days.

(21) Appl. No.: 17/312,734

(22) PCT Filed: Dec. 9, 2019

(86) PCT No.: PCT/IN2019/050896
§ 371 (c)(1),
(2) Date: Jun. 10, 2021

(87) PCT Pub. No.: WO2020/121321
PCT Pub. Date: Jun. 18, 2020

(65) Prior Publication Data
US 2022/0048917 A1   Feb. 17, 2022

(30) Foreign Application Priority Data
Dec. 11, 2018   (IN) .............................. 201811046767

(51) Int. Cl.
*C07D 487/04* (2006.01)
*B01J 31/22* (2006.01)
*B01J 31/24* (2006.01)

(52) U.S. Cl.
CPC ........ *C07D 487/04* (2013.01); *B01J 31/2295* (2013.01); *B01J 31/2409* (2013.01); *B01J 2231/645* (2013.01); *B01J 2531/822* (2013.01)

(58) Field of Classification Search
CPC . C07D 487/04; B01J 31/2295; B01J 31/2409; B01J 2231/645; B01J 2531/822
(Continued)

(56) References Cited

FOREIGN PATENT DOCUMENTS

WO   2005097733 A1   10/2005

OTHER PUBLICATIONS

Sigma-Aldrich, Alumina, ProductInformation, Sep. 12, 1998, pp. 1-2.. (Year: 1998).*

(Continued)

*Primary Examiner* — Taylor V Oh
(74) *Attorney, Agent, or Firm* — Dinsmore & Shohl LLP

(57) ABSTRACT

The present invention provides highly efficient process for the preparation of enantiomerically enriched Sitagliptin of Formula (Ia). More particularly, a direct rhodium catalyzed asymmetric hydrogenation in the presence of bis-phosphine chiral ligand has been developed to yield enantiopure Sitagliptin product with the highest enantiomeric excess of 85-99.9%.

Formula Ia

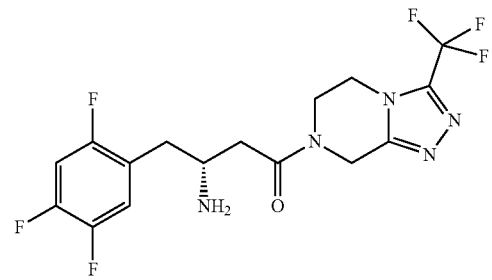

7 Claims, 3 Drawing Sheets

(58) Field of Classification Search
USPC .......................................................... 544/350
See application file for complete search history.

(56) References Cited

OTHER PUBLICATIONS

Hansen, et al., "First Generation Process for the Preparation of the DPP-IN Inhibitor Sitagliptin", Organic Process Research & Development, vol. 9, pp. 634-639, 2005.
Steinhuebel, et al., "Direct Asymmetric Reductive Amination", JACS Communications, vol. 131, pp. 113616-11317, 2009.
Hansen, et al., "Highly Efficient Asymmetric Synthesis of Sitagliptin", JACS Articles, vol. 131, pp. 8798-8804, 2009.
Dong, et al., "A Convenient Route to Substituted Tetrahydrafuran-3-ones: Condensations of a-Bromo Ketones with Aromatic Aldehydes", vol. 35, No. 50, pp. 9367-9370, 1994.

* cited by examiner

HIGHLY EFFICIENT PROCESS FOR THE PREPARATION OF SITAGLIPTIN VIA RHODIUM CATALYZED ASYMMETRIC HYDROGENATION

CROSS-REFERENCES TO RELATED APPLICATIONS

This application is a national-stage application under 35 U.S.C. § 371 of International Application No. PCT/IN2019/050896, filed Dec. 9, 2019, which International Application claims benefit of priority to Indian Application No. 201811046767, filed Dec. 11, 2018.

TECHNICAL FIELD

The present disclosure provides highly efficient process for the preparation of enantiomerically enriched Sitagliptin. More particularly, a direct rhodium catalyzed asymmetric hydrogenation in the presence of bis-phosphine chiral ligand has been developed to yield enantiopure Sitagliptin product with the highest enantiomeric excess of 85-99.9%.

BACKGROUND

Beta amino acids and its derivatives have lot of medicinal significance. Beta amino acids are also present in peptides and different heterocycles. In beta amino acids, the amino group is linked to the beta carbon. Different free forms and derivatives of beta amino acid exhibit interesting pharmacological effects. Many methods of syntheses and transformations have been explored to obtain enantiomerically pure product of beta amino acid derivative. Still it is a challenge in organic synthesis to develop a process for the preparation of beta amino acids with high enantiomeric excess, when different functional groups are bonded to the beta carbon in order to maintain the chirality.

Many API's exhibiting antibiotic, antifungal, cytotoxic, and other pharmacological properties comprise the product of the present disclosure, a chiral beta-amino acid derivatives. They are therefore frequently used chiral building blocks in organic synthesis.

Another important application is the substitution of unnatural alpha- and beta-amino acids in biologically active peptides, which greatly enhance the understanding of enzyme mechanisms, protein conformations and properties related to molecular recognition, and for obtaining peptides with increased potency and enzymatic stability.

More preferably, here the beta amino acid compound is Sitagliptin Formula Ia. Sitagliptin is chemically known as (R)-4-oxo-4-[3-(trifluoromethyl)-5,6-dihydro[1,2,4]triazolo-[4,3-a]pyrazin-7(8H)-yl]-1-(2,4,5-trifluorophenyl)butan-2-amine and marketed as a phosphate salt under trade name JANUVIA by Merck.

Formula Ia

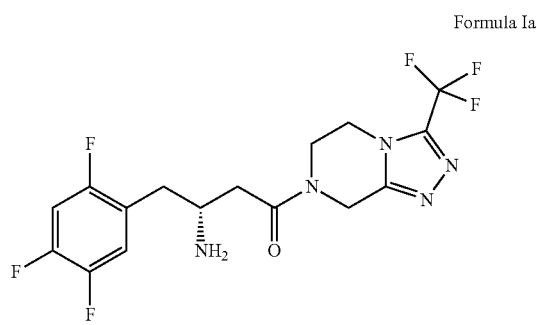 [SMILES: N[C@@H](CC(=O)N1CCn2c(nnc2C(F)(F)F)C1)Cc1cc(F)c(F)cc1F]

Sitagliptin is used possibly with other medications to control high blood sugar. It is used in people with type 2 diabetes. Controlling high blood sugar helps prevent kidney damage, blindness, nerve problems, loss of limbs, and sexual function problems. Proper control of diabetes may also lessen your risk of a heart attack or stroke. Sitagliptin is a diabetes drug that works by increasing levels of natural substances called incretins. Incretins help to control blood sugar by increasing insulin release, especially after a meal. It also decreases the amount of sugar in liver.

J. Org. Process Res. Dev. 2005, 9, 634-639 describes lengthy multi step reaction process giving only 52% yield of sitagliptin. However, in this transformation selective separation of (E/Z) isomers was problematic as well as overall approach was multi-step.

J. Am. Chem. Soc. 2009, 131(32): p. 11316-11317 reports direct asymmetric reductive amination to sitagliptin with 96% yield and 99.5% enantiomeric excess, which is achieved by using Ruthenium metal and (R)-dm-segphos as ligand in presence of acidic additives like acetic acid, benzoic acid, salicylic acid, chloroacetic acid etc.

PCT application WO2005097733 describes the process for the preparation of beta amino acid derivatives including sitagliptin using Ru catalyst in the presence of chiral mono- or bis-phosphene ligands. But this application specifically does not include ferrocenyl bisphosphene ligands with Ru catalyst for asymmetric hydrogenation, in its description.

Sitagliptin is an important active ingredient for diabetic patients. Therefore, highly enantioselective, low cost synthesis of this API is always in need. The present disclosure provides such atom economic single step protocol like asymmetric hydrogenation which provides an unprecedented enantiomeric excess of 90% and above. It reduces the cost of the process also by generating the desired active catalyst in-situ, circumventing the need of separate synthesis and isolation of active catalyst.

Main objectives of the present disclosure are to provide a highly efficient process for the preparation of enantiomerically enriched Sitagliptin.

Another objective of the present disclosure is to provide a direct rhodium catalyzed asymmetric hydrogenation in the presence of bis-phosphine chiral ligand to yield enantiopure Sitagliptin product with the highest enantiomeric excess of 85-99.9%.

An another objective of the present disclosure is to provide process for the preparation of beta amino acid derivatives of Formula (I), more preferably Sitagliptin of Formula (Ia), via highly enantioselective asymmetric hydrogenation with in-situ generated catalyst by using Rh-catalyst in the presence of ferrocenyl bisphosphene ligands, which provides enantiopure Sitagliptin of Formula (Ia) with the highest enantiomeric excess of 85-99.9%.

SUMMARY

Accordingly, the present disclosure relates to a process for the preparation of sitagliptin, compound of Formula (Ia) by enantioselective asymmetric hydrogenation of dehydrositagliptin of Formula (IIa) employing rhodium catalyst on bisphosphine ferrocenyl ligands of Formula L, to obtain enantiomeric excess in the range of 85-99.9%;

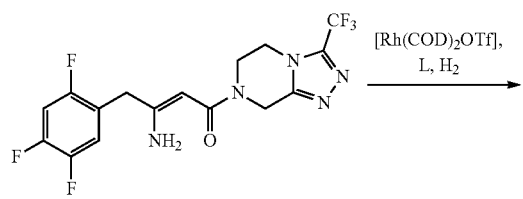
Dehydrositagliptin (IIa)
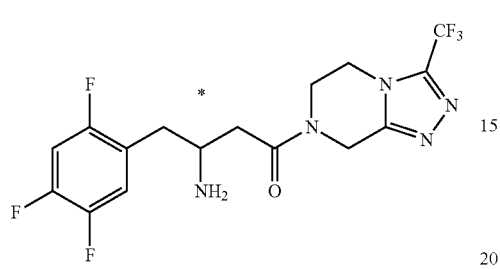
Formula Ia
said bisphosphine ferrocenyl ligands are selected from the group consisting of Formula L1-L8 are:
(a) L1:
1,2-bis(2,5-dimethylphospholan-1-yl)benzene
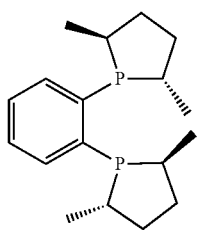
L1
(b) L2: (2,2-dimethyl-1,3-dioxolane-4,5-diyl)bis(diphenylphosphane)
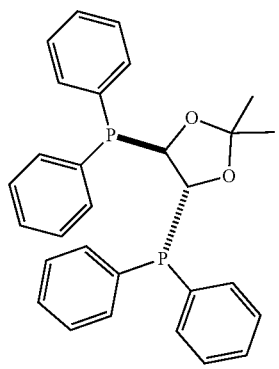
L2
(c) L3: 1,1'-Bis[2,5-dimethylphospholano]ferrocene
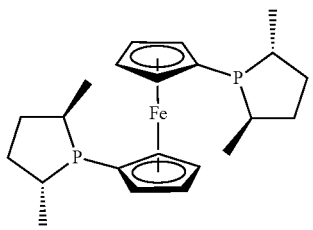
L3
(d) L4: butane-2,3-diylbis(diphenylphosphane)
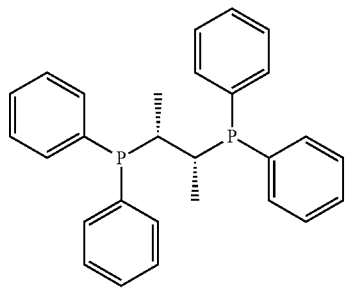
L4
(e) L5:
1,2-bis(2,5-diisopropylphospholan-1-yl)benzene
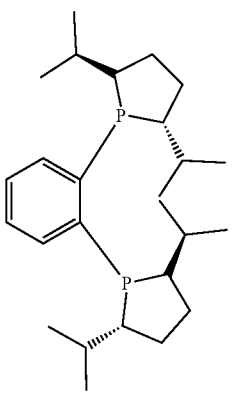
L5

(f) L6: 1,1'-Bis[2,5-diethylphospholano]ferrocene

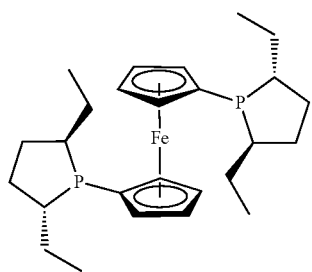

(g) L7: 1,1'-Bis(2,5-di-isopropylphospholano)ferrocene

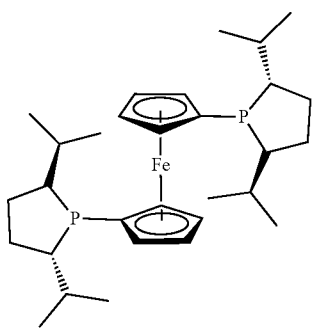

(h) L8: 1,1'-Bis((2,5)-2,5-di-ter-butylphospholano)ferrocene

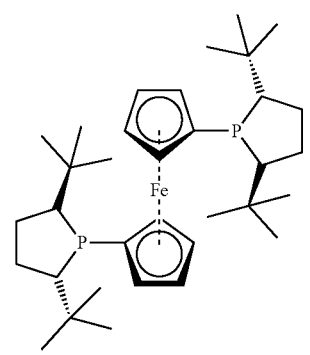

wherein, the process for the preparation of sitagliptin, compound of Formula (Ia) comprises the steps of:
(i) mixing compound of Formula (IIa) with rhodium catalyst, ferrocenyl bisphosphine ligand L, and additive to obtained reaction mixture;
(ii) adding solvent in the reaction mixture of step i) in the inert atmosphere of argon and stirring at a temperature of 25° C. for an hour to obtained reaction slurry;
(iii) maintaining the reaction slurry as obtained in step ii) under hydrogen pressure of 10-30 bar at a temperature of 35° C.-90° C. for 17-24 hrs into autoclave followed by cooling at a temperature of 25° C. of step iii) and releasing the pressure to obtained reaction mixture 2;
(iv) passing the reaction mixture 2 of step iii) through neutral alumina bed followed by collecting the filtrate and drying the residue to afford compound of Formula (Ia).

In an embodiment, as described herein, the rhodium catalyst is [Rh(COD)$_2$OTf].

In another embodiment, as described herein, the additive is selected from the group consisting of salicylic acid, acetic acid, ammonium chloride, phosphoric acid, ammonium salicylate, tetramethyl ammonium iodide, tetraethyl ammonium iodide, tetra butyl ammonium bromide, butyl phosphoric acid, dibutyl phosphate, tributyl phosphate.

In yet another embodiment, the solvent selected from the group consisting of methanol, dichloromethane, tetrahydrofuran, trifluoroethanol, toluene, 1,4-dioxane and ethyl acetate.

In another embodiment, the preparation of beta amino acid derivatives of Formula (I), more preferably Sitagliptin of Formula (Ia), with the highest enantiomeric excess of 85-99.9%,

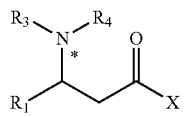

Formula I wherein, the carbon atom marked with an '*' is enantiomerically enriched;

X is OR$_2$, SR$_2$, or NR$_2$R$_2$';

R$_1$ is alkyl, aryl, heteroaryl, aralkyl, or optionally substituted heteroaryl;

R$_2$ and R$_2'$ are each independently selected from the group comprising of hydrogen, alkyl, aryl, aralkyl; or R$_2$ and R$_2'$ together with the nitrogen atom to which they are attached may form a 4- to 7-membered optionally substituted ring system optionally containing an additional heteroatom selected from O, S, N, NH, and NC$_{1-4}$ alkyl; and said heterocyclic ring system being optionally fused with a 5- to 6-membered saturated or aromatic carbocyclic ring system or 5- to 6-membered saturated or aromatic heterocyclic ring system containing one to three heteroatoms selected from O, S, N, NH, and NC$_{1-4}$ alkyl, said fused ring system being unsubstituted or substituted;

R$_3$ and R$_4$ are independently selected from the group comprising of —H, alkyl, —COCH$_3$.

The process, as described herein, relates to a highly enantioselective rhodium metal catalyzed asymmetric hydrogenation of a prochiral enamine of compound of structural Formula II in the presence of bisphosphine ferrocenyl ligand of Formula L to provide chiral beta amino acid derivatives of structural Formula I, more preferably compound of Formula Ia.

(II)

In still another embodiment, the bisphosphine ferrocenyl ligand of Formula L is selected from the group of ligands L1-L8;
(a) L1: 1,2-bis(2,5-dimethylphospholan-1-yl)benzene
(b) L2: (2,2-dimethyl-1,3-dioxolane-4,5-diyl)bis(diphenylphosphane)
(c) L3: 1,1'-Bis[2,5-dimethylphospholano]ferrocene
(d) L4: butane-2,3-diylbis(diphenylphosphane)
(e) L5: 1,2-bis(2,5-diisopropylphospholan-1-yl)benzene
(f) L6: 1,1'-Bis[2,5-diethylphospholano]ferrocene
(g) L7: 1,1'-Bis(2,5-di-isopropylphospholano)ferrocene
(h) L8: 1,1'-Bis((2,5)-2,5-di-ter-butylphospholano)ferrocene In yet another embodiment, the present embodiment provides general process for the preparation of Sitagliptin, compound of Formula Ia. Asymmetric hydrogenation of dehydrositagliptin to sitagliptin of Formula Ia is shown below in synthetic scheme 1.

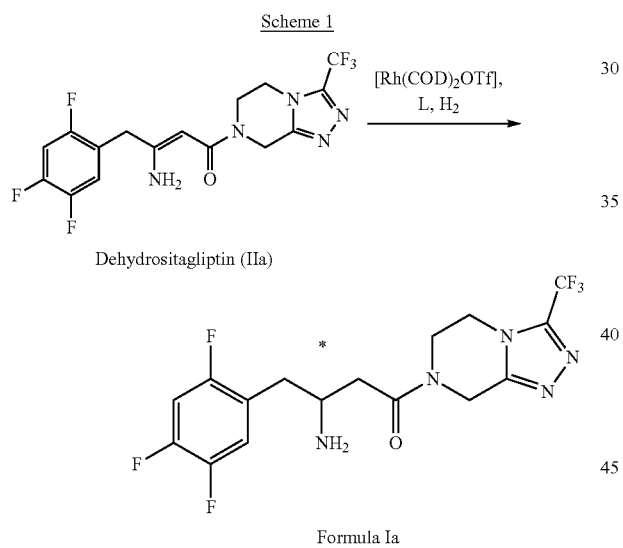

DETAILED DESCRIPTION

Figure 1:
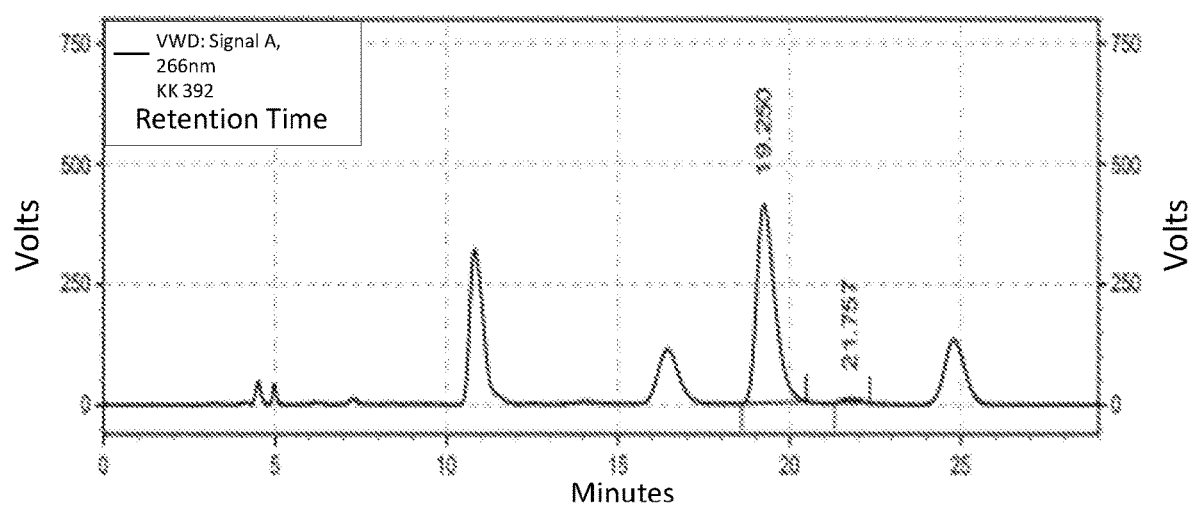
FIG. 1 describes HPLC chromatogram of enantiopure sitagliptin.
Figure 2:
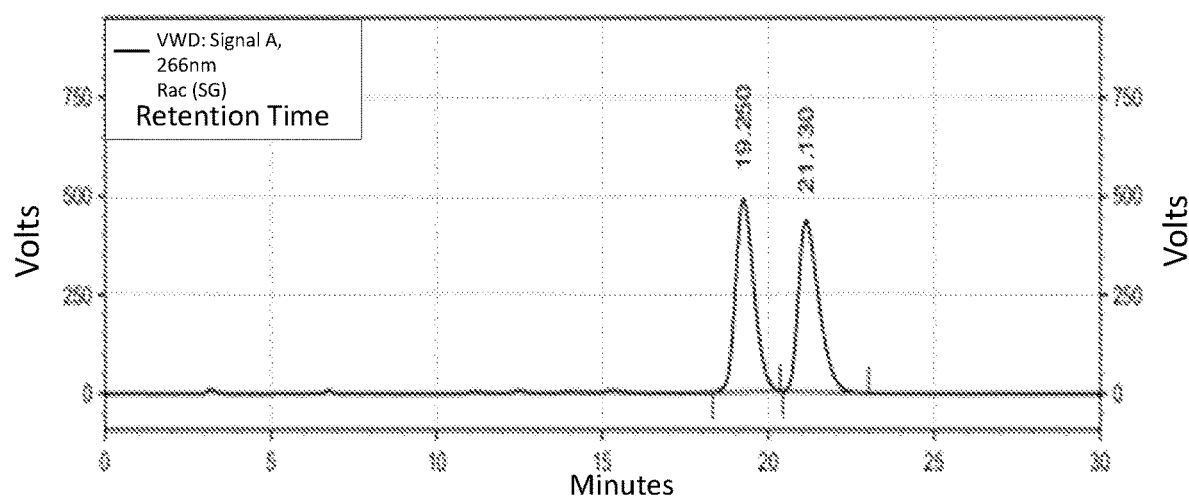
FIG. 2 relates to the HPLC chromatogram of racemic sitagliptin.
Figure 3:
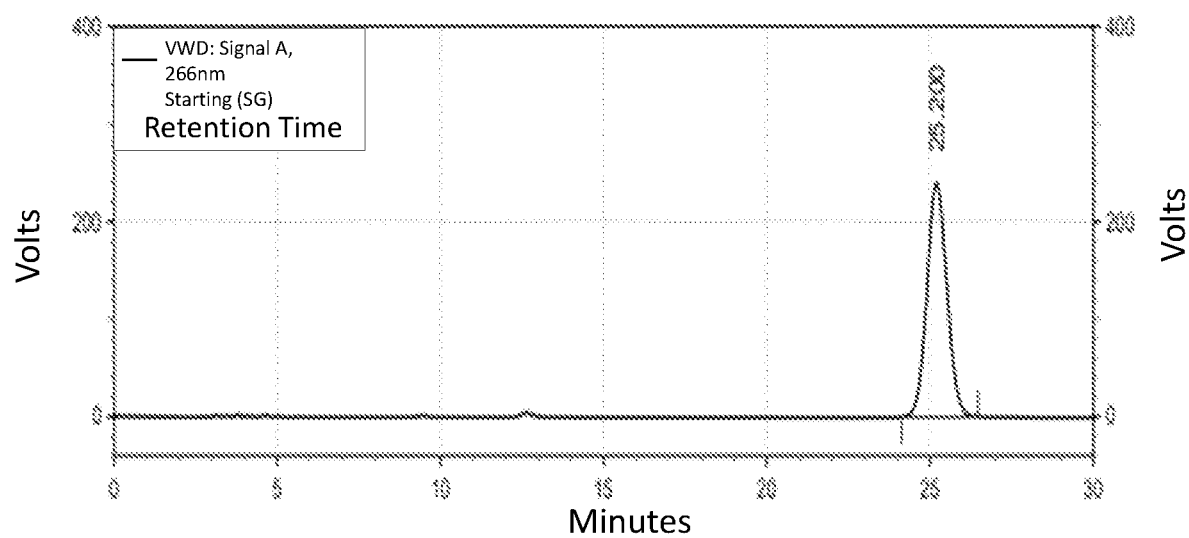
FIG. 3 describes the HPLC chromatogram of dehydrositagliptin.

It is to be understood that the figures, schemes and descriptions of the present disclosure have been simplified to illustrate elements that are relevant for a clear understanding of the disclosure. The detailed description will be provided herein below with reference to the attached drawings, and schemes.

In view of the above, the present disclosure provides a process for the preparation of beta amino acid derivatives of Formula (I), more preferably Sitagliptin of Formula (Ia), with the highest enantiomeric excess of 85-99.9%, Formula I

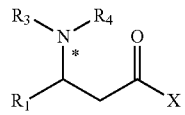

wherein, the carbon atom marked with an '*' is enantiomerically enriched;

X is $OR_2$, $SR_2$, or $NR_2R_2'$;

$R_1$ is alkyl, aryl, heteroaryl, aralkyl, or optionally substituted heteroaryl;

$R_2$ and $R_2'$ are each independently selected from the group comprising of hydrogen, alkyl, aryl, aralkyl; or $R_2$ and $R_2'$ together with the nitrogen atom to which they are attached may form a 4- to 7-membered optionally substituted ring system optionally containing an additional heteroatom selected from O, S, N, NH, and $NC_{1-4}$ alkyl; and said heterocyclic ring system being optionally fused with a 5- to 6-membered saturated or aromatic carbocyclic ring system or 5- to 6-membered saturated or aromatic heterocyclic ring system containing one to three heteroatoms selected from O, S, N, NH, and $NC_{1-4}$ alkyl, said fused ring system being unsubstituted or substituted;

$R_3$ and $R_4$ are independently selected from the group comprising of —H, alkyl, —$COCH_3$.

The process, as described herein, relates to a highly enantioselective rhodium metal catalyzed asymmetric hydrogenation of a prochiral enamine of compound of structural Formula II in the presence of bisphosphine ferrocenyl ligand of Formula L to provide chiral beta amino acid derivatives of structural Formula I, more preferably compound of Formula Ia.

(II)

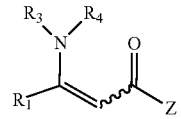

The general process to afford compound of Formula (I) comprises of following steps;
(i) mixing compound of formula II with rhodium catalyst, ferrocenyl bisphosphine ligand L, and additive;
(ii) adding suitable solvent in the reaction mixture of step (i) in the inert atmosphere of argon and stirring at suitable temperature for an hour;
(iii) maintaining the reaction mixture under suitable hydrogen pressure at suitable temperature for 24 hrs into autoclave;
(iv) cooling the reaction mixture to a temperature in the range of 25-35° C. of step (iii) and releasing the pressure;
(v) passing the reaction mixture through neutral alumina bed;
(vi) collecting the filtrate and drying the residue to afford compound of Formula (I).

More particularly, the present embodiment provides above general process for the preparation of Sitagliptin, compound of Formula Ia. Asymmetric hydrogenation of dehydrositagliptin to sitagliptin of Formula Ia is shown below in synthetic scheme-1.

Scheme 1

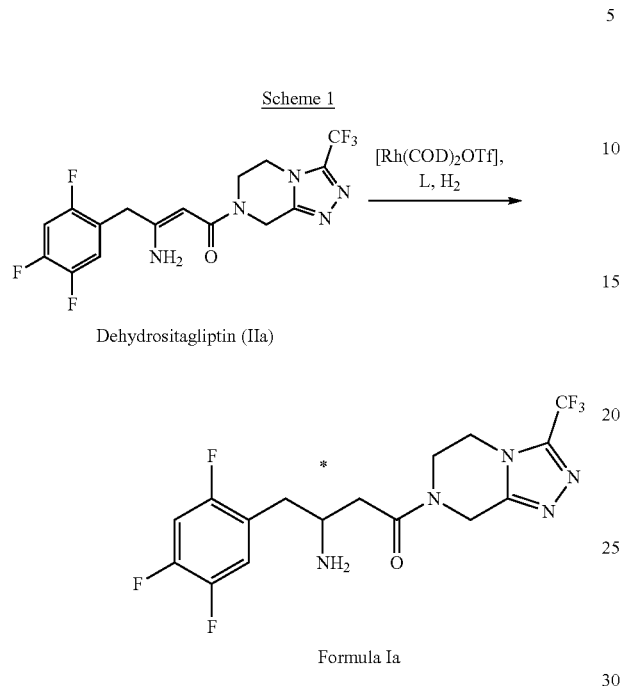

Dehydrositagliptin (IIa)

Formula Ia

The bisphosphine ferrocenyl ligand of Formula L is selected from the group of ligands L1-L8 represented below;

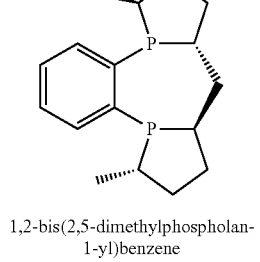

L1

1,2-bis(2,5-dimethylphospholan-1-yl)benzene

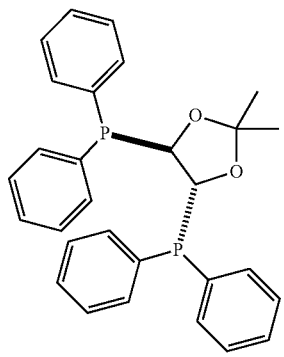

L2

(2,2-dimethyl-1,3-dioxolane-4,5-diyl)bis(diphenylphosphane)

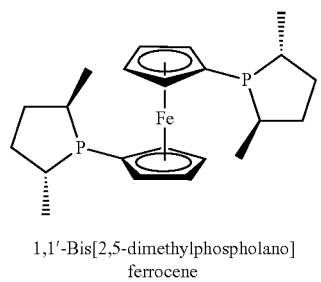

L3

1,1′-Bis[2,5-dimethylphospholano]ferrocene

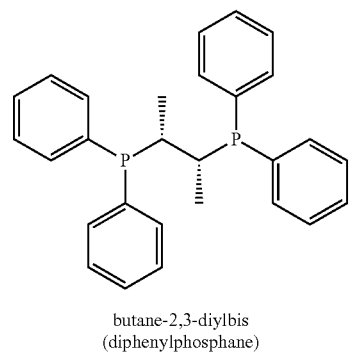

L4 butane-2,3-diylbis(diphenylphosphane)

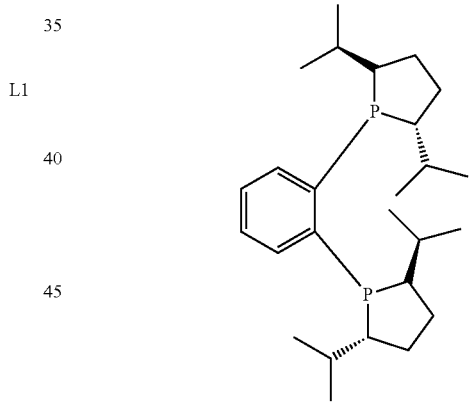

L5

1,2-bis(2,5-diisopropylphospholan-1-yl)benzene

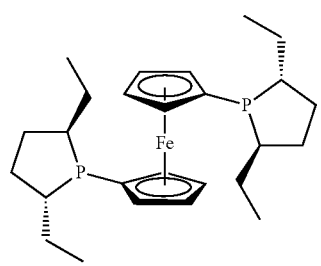

L6

1,1′-Bis[2,5-diethylphospholano]ferrocene

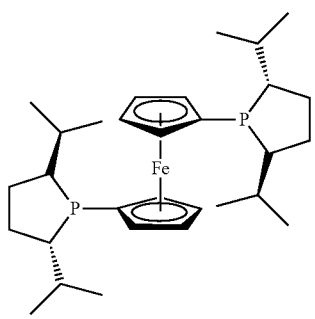

1,1'-Bis(2,5-di-isopropylphospholano)ferrocene
L7

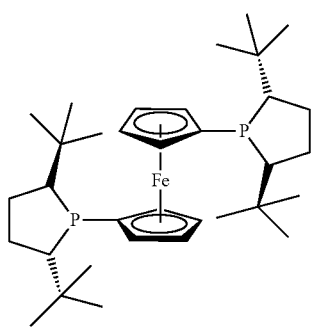

1,1'-Bis((2,5)-2,5-di-ter-butylphospholano)ferrocene
L8

In an aspect of the present embodiment involves a an additives at step (i) of the process, which may be selected from the group comprising of Salicylic acid, Acetic acid, Ammonium chloride, Phosphoric acid, Ammonium salicylate, Tetra methyl ammonium iodide, Tetraethyl ammonium iodide, Tetra butyl ammonium bromide, Butyl phosphoric acid, Dibutyl phosphate, Tributyl phosphate.

Another aspect of the present embodiment involves a suitable solvent at step (ii) of the process, suitable solvents may include alcohol solvents. Alcohol solvents, which may include methanol, ethanol, isopropanol, or mixtures thereof. In particularly useful embodiments, methanol is used as a solvent at step (ii).

Suitable temperature for stirring the reaction mass at step (ii) may be 20° C.-40° C., more preferably 25° C.-35° C.

Suitable temperature for maintaining the reaction mixture at step (iii) may be 35° C.-95° C., preferably 60° C.-80° C., more preferably 70°–80° C.

Suitable hydrogen pressure for maintaining reaction mixture at step (iii) may be 20 bar-40 bar, more preferably 30 bar.

Asymmetric hydrogenation of dehydrositagliptin is carried out using bis-phosphine ligands of Formulas L1 to L8, as shown above, with Rh precursor [Rh(COD)$_2$OTf]. Several experiments have been conducted by using different reaction parameters and ligands L1 to L8. Results of these experiments are summarized in Table 1.

TABLE 1

Rhodium catalyzed asymmetric hydrogenation of dehydrositagliptin to sitagliptin.$^a$

| Ex. No. | Ligand | Solvent | Press (bar) | Additives | Temp (° C.) | Time (hrs) | Conv (%) | ee (%) |
|---|---|---|---|---|---|---|---|---|
| Ligand Screening | | | | | | | | |
| 1 | L1 | Methanol | 20 | NH$_4$Cl | 50 | 17 | 00 | 00 |
| 2 | L2 | Methanol | 20 | NH$_4$Cl | 50 | 17 | 00 | 00 |
| 3 | L3 | Methanol | 20 | NH$_4$Cl | 50 | 17 | 20 | 85 |
| 4 | L4 | Methanol | 20 | NH$_4$Cl | 50 | 17 | 00 | 00 |
| Solvent Screening | | | | | | | | |
| 5 | L3 | Methanol | 20 | NH$_4$Cl | 60 | 18 | 30 | 85 |
| 6 | L3 | DCM | 20 | NH$_4$Cl | 60 | 18 | 00 | 00 |
| 7 | L3 | THF | 20 | NH$_4$Cl | 60 | 18 | 00 | 00 |
| 8 | L3 | TFE | 20 | NH$_4$Cl | 60 | 18 | 6 | 2 |
| 9 | L3 | Toluene | 20 | NH$_4$Cl | 60 | 18 | 00 | 00 |
| 10 | L3 | 1,4-dioxane | 20 | NH$_4$Cl | 60 | 18 | 00 | 00 |
| 11 | L3 | EtOAc | 20 | NH$_4$Cl | 60 | 18 | 00 | 00 |
| Temperature Screening | | | | | | | | |
| 12 | L3 | Methanol | 20 | NH$_4$Cl | 50 | 17 | 20 | 85 |
| 13 | L3 | Methanol | 20 | NH$_4$Cl | 60 | 17 | 30 | 85 |
| 14 | L3 | Methanol | 20 | NH$_4$Cl | 70 | 17 | 68 | 87 |
| 15 | L3 | Methanol | 20 | NH$_4$Cl | 80 | 17 | 80 | 88 |
| 16 | L3 | Methanol | 20 | NH$_4$Cl | 90 | 17 | 90 | 80 |
| Pressure Screening | | | | | | | | |
| 17 | L3 | Methanol | 10 | NH$_4$Cl | 70 | 24 | 00 | 00 |
| 18 | L3 | Methanol | 20 | NH$_4$Cl | 70 | 24 | 30 | 85 |
| 19 | L3 | Methanol | 30 | NH$_4$Cl | 70 | 24 | 90 | 87 |
| Additive Screening | | | | | | | | |
| 20 | L3 | Methanol | 30 | NH$_4$Cl | 70 | 24 | 90 | 87 |
| 21 | L3 | Methanol | 30 | CH$_3$CO$_2$H | 70 | 24 | 74 | 85 |
| 22 | L3 | Methanol | 30 | H$_3$PO$_4$ | 70 | 24 | 94 | 88 |
| 23 | L3 | Methanol | 30 | — | 70 | 24 | 50 | 90 |

TABLE 1-continued

Rhodium catalyzed asymmetric hydrogenation of dehydrositagliptin to sitagliptin.[a]

| Ex. No. | Ligand | Solvent | Press (bar) | Additives | Temp (° C.) | Time (hrs) | Conv (%) | ee (%) |
|---|---|---|---|---|---|---|---|---|
| Screening of Additives | | | | | | | | |
| 24 | L6 | Methanol | 30 | — | 70 | 24 | 32 | 79 |
| 25 | L6 | Methanol | 30 | $NH_4Cl$ | 70 | 24 | 30 | 84 |
| 26 | L6 | Methanol | 30 | Acetic acid | 70 | 24 | 20 | 84 |
| 27 | L6 | Methanol | 30 | $H_3PO_4$ | 70 | 24 | 30 | 86 |
| 28 | L6 | Methanol | 30 | Salicylic acid | 70 | 24 | 69 | 85 |
| Screening of temperature | | | | | | | | |
| 29 | L6 | Methanol | 30 | Salicylic acid | 70 | 24 | 69 | 85 |
| 30 | L6 | Methanol | 30 | Salicylic acid | 80 | 24 | 98 | 86 |
| Screening of catalyst loading | | | | | | | | |
| 31 | L6 1 mol % | Methanol | 30 | $NH_4Cl$ | 70 | 24 | 65 | 84 |
| 32 | L6 2 mol % | Methanol | 30 | $NH_4Cl$ | 70 | 24 | 90 | 88 |
| 33 | L6 3 mol % | Methanol | 30 | $NH_4Cl$ | 70 | 24 | 91 | 85 |
| 34 | L6 4 mol % | Methanol | 30 | $NH_4Cl$ | 70 | 24 | 99 | 85 |
| 35 | L6 5 mol % | Methanol | 30 | $NH_4Cl$ | 70 | 24 | 99 | 85 |
| Screening of Additives | | | | | | | | |
| 36 | L7 1 mol % | Methanol | 30 | — | 60 | 18 | 10 | 80 |
| 37 | L7 1 mol % | Methanol | 30 | Salicylic acid | 60 | 18 | 70 | 90 |
| 38 | L7 1 mol % | Methanol | 30 | Acetic acid | 60 | 18 | 10 | 94 |
| 39 | L7 1 mol % | Methanol | 30 | $NH_4Cl$ | 60 | 18 | 30 | 91 |
| 40 | L7 1 mol % | Methanol | 30 | $H_3PO_4$ | 60 | 18 | 5 | 87 |
| 41 | L7 1 mol % | Methanol | 30 | Ammonium salicylate | 60 | 18 | 20 | 89 |
| 42 | L7 1 mol % | Methanol | 30 | Tetramethyl ammonium iodide | 60 | 18 | — | — |
| 43 | L7 1 mol % | Methanol | 30 | Tetraethyl ammonium iodide | 60 | 18 | — | — |
| 44 | L7 1 mol % | Methanol | 30 | Tetra butyl ammonium bromide | 60 | 18 | — | — |
| 45 | L7 1 mol % | Methanol | 30 | Butyl phosphoric acid | 70 | 24 | 34 | 89 |
| 46 | L7 1 mol % | Methanol | 30 | Dibutyl phosphate | 70 | 24 | 63 | 90 |
| 47 | L7 1 mol % | Methanol | 30 | Tributyl phosphate | 70 | 24 | 5 | 83 |
| 48 | L7 1 mol % | Methanol | 30 | Formic acid | 70 | 24 | 15 | 89 |
| 49 | L7 1 mol % | Methanol | 30 | Sodium benzoate | 70 | 24 | 10 | 66 |
| 50 | L7 1 mol % | Methanol | 30 | Pyridinium p-toluene sulphate | 70 | 24 | 14 | 80 |
| 51 | L7 1 mol % | Methanol | 30 | Salicylic acid | 70 | 18 | 95 | 92 |
| 52 | L7 1 mol % | Methanol | 30 | Salicylic acid | 60 | 18 | 95 | 94 |
| 53 | L7 1 mol % | Methanol | 30 | Salicylic acid | 50 | 18 | 90 | 95 |
| 54 | L7 1 mol % | Methanol | 30 | Salicylic acid | 45 | 18 | 85 | 98 |
| 55 | L7 1 mol % | Methanol | 30 | Salicylic acid | 40 | 18 | 60 | 95 |

TABLE 1-continued

Rhodium catalyzed asymmetric hydrogenation of dehydrositagliptin to sitagliptin.[a]

| Ex. No. | Ligand | Solvent | Press (bar) | Additives | Temp (° C.) | Time (hrs) | Conv (%) | ee (%) |
|---|---|---|---|---|---|---|---|---|
| 56 | L7 1 mol % | Methanol | 30 | Salicylic acid | 35 | 18 | 10 | 96 |

[a]Conditions: Substrate (dehydrositagliptin) 85.11 mg; [Rh(COD)$_2$OTf]: 1 mg (1 mol %); Ligand/Rh: 1.1; Additive/Rh: 1; Solvent: 2 ml; conversion and enantiomeric excess is determined by chiral HPLC.

General Information

All manipulations were carried out under an inert atmosphere of argon using standard Schlenk line techniques or m-Braun glove box. Solvents were dried by standard procedures unless otherwise mentioned. Ferrocene bis-phosphine ligands and [Rh(COD)$_2$OTf] were purchased from Sigma-Aldrich. While 1,1'-Bis(2,5-di-isopropylphospholano)ferrocene was purchased from Stream chemicals. Hydrogen gas (H$_2$) was supplied by Ms. Vadilal Chemicals Ltd., Pune, India. All other reagents/chemicals, solvents were purchased from local suppliers (Spectrochem Pvt. Ltd.; Avra Synthesis Pvt. Ltd.; Thomas Baker Pvt. Ltd. etc). Asymmetric hydrogenation was performed in Amar Equipment Pvt. Ltd. high-pressure reactor equipped with pressure regulators and safety rupture valve.

Solution NMR spectra were recorded on a Bruker Advance 200, 400 and 500 MHz instruments at 298 K unless mentioned otherwise. Chemical shifts are referenced to external reference TMS ($^1$H). Coupling constants are given as absolute values. Multiplicities are given as follows s: singlet, d: doublet, t: triplet, m: multiplet. The enantiomeric excess and conversion to sitagliptin was determined by chiral HPLC on an Agilent Technologies 1260 Infinity instrument with Chiralpak IC column (250 mm×4.6 mm×5 µm).

The following high performance liquid chromatographic (HPLC) conditions were used to determine percent conversion to product & optical purity of the sitagliptin product:
Column: Chiral Pak IC (250 mm×4.6 mm×5 µm)
Eluent: n-Hexane: Ethanol: Diethyl amine (80:20:0.1)
Gradient: Isocratic
Flow rate: 1 ml/min
Injection volume: 10 µL,
UV detection: 266 nm
Column temp.: ambient
Retention times: RT's may vary by ±0.5 min
Dehydrositagliptin: 24.793 min
Racemic: 19.25 min & 21.757 min
Impurity: 16.440 min
Salicylic acid: 10.810 min

EXAMPLES

The following examples, which include preferred embodiments, will serve to illustrate the practice of this disclosure, it being understood that the particulars shown are by way of example and for purpose of illustrative discussion of preferred embodiments as described herein.

Example-1

General Process for the Synthesis of Sitagliptin from Dehydrositagliptin

In a 5 mL reaction vial equipped with septa and inlet needle, dehydrositagliptin (100 eq. 85.11 mg), [Rh(COD)$_2$OTf] (1 eq. 1 mg), ligand L (1.05 eq.) and additive (1 eq.) were added in the glove box. Reaction vial was then transferred in a large Schlenk type container and was then taken out from the glove box. 2 mL dry methanol was added to the vial in inert atmosphere and the resultant reaction slurry was stirred for 1 hour at 25° C. After that, the reaction vial was kept in an autoclave and the autoclave was purged three times by using hydrogen gas pressure (40 bars). Finally, the autoclave was pressurized to 30 bar of hydrogen pressure and the hydrogenation was continued at 50-70° C. for 18 hrs. Then autoclave was cooled to 25° C., excess pressure was released and the autoclave was opened. The vials were taken out from autoclave reactor. The thus obtained reaction mixture was passed through neutral alumina bed, the filtrate was collect and dried to yield residue. The resultant residue was then analyzed by HPLC or NMR spectroscopy. $^1$H NMR (400 MHz CDCl$_3$) δ=7.10 (m, 1H), 6.89 (m, 1H), 4.89 (s, 2H), 4.21 (t, 2H) 4.06 (t, 2H), 3.36 (t, 1H), 3.25 (t, 1H), 2.79 (s, 1H), 2.32 (t, 1H), 2.00 (t, 1H).

HPLC: (Ref: FIG. 1)

| | VWD: Signal A, 266 nm Results | | | |
|---|---|---|---|---|
| Retention Time | Area | Area % | Height | Height % |
| 20.53 | 129681411 | 98.78 | 3064393 | 98.27 |
| 23.35 | 1604318 | 1.22 | 53969 | 1.73 |
| Totals | 131285729 | 100.00 | 3118362 | 100.00 |

Example-2

Process for the Synthesis of Sitagliptin from Dehydrositagliptin Using Ligand of Formula L3

In a 5 ml reaction vial equipped with septa and inlet needle, dehydrositagliptin (100 eq. 85.11 mg), [Rh(COD)$_2$OTf] (1 eq. 1 mg), ligand L3 (1.05 eq.) and additive (1 eq.) were added in the glove box. Reaction vial was then kept in a large Schlenk type container and was then taken out from the glove box. 2 mL dry methanol was added to the vial in inert atmosphere and the resultant reaction slurry was stirred for 1 hour at 25° C. After that, the reaction vial was kept in an autoclave and the autoclave was purged three times by using hydrogen gas pressure (40 bars). Finally, the autoclave was pressurized to 30 bar hydrogen pressure and the hydrogenation was continued at 70° C. for 18 hrs period. After 18 hrs, the autoclave was cooled to 25° C., excess pressure was released and the autoclave was opened. The vials were taken out from autoclave reactor. The thus obtained reaction mixture was passed through neutral alumina bed, the filtrate was collect and dried to yield residue. The resultant residue was then analyzed by HPLC or NMR spectroscopy.

Example-3

Process for the Synthesis of Sitagliptin from Dehydrositagliptin Using Ligand of Formula L7

In a 5 ml reaction vial equipped with septa and inlet needle, dehydrositagliptin (100 mol %, 85.11 mg), [Rh(COD)$_2$OTf] (1 mol %), ligand L7 (1.1 mol %.) and additive (150 mol %) were added in the glove box. Reaction vial was then kept in a large Schlenk type container and was then taken out from the glove box. 2 ml dry methanol was added to the vial in inert atmosphere and the resultant reaction slurry was stirred for 1 hour at 25° C. After that reaction vial was kept in an autoclave and the autoclave was purged three times by using hydrogen gas pressure (40 bars). Finally, the autoclave was pressurized to 30 bar hydrogen pressure and the hydrogenation was continued at 50° C. for 18 hrs period. After 18 hrs, the autoclave was cooled to 25° C., excess pressure was released and the autoclave was opened. The vials were taken out from autoclave reactor. The thus obtained reaction mixture was passed through neutral alumina bed, the filtrate was collect and dried to yield residue. The resultant residue was then analyzed by HPLC or NMR spectroscopy.

ADVANTAGES

Atom economic single step protocol of process

An unprecedented enantiomeric excess of 85-99.9% is observed

The desired active catalyst is in-situ generated, circumventing the need of separate synthesis and isolation of active catalyst Sitagliptin presented in Formula (Ia) is a new class of oral anti-hyperglycemic drug known as a DPP-4 inhibitor or incretin enhancer for the treatment of Type 2 diabetes mellitus (T2DM)

Sitagliptin can also be used in combination drugs without any adverse effects.

We claim:

1. A process for preparation of sitagliptin compound of Formula (Ia):

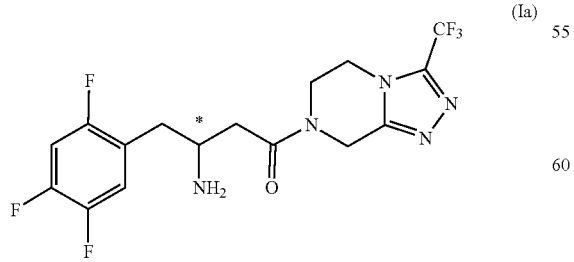

(Ia)

by enantioselective asymmetric hydrogenation of dehydrositagliptin of Formula (IIa):

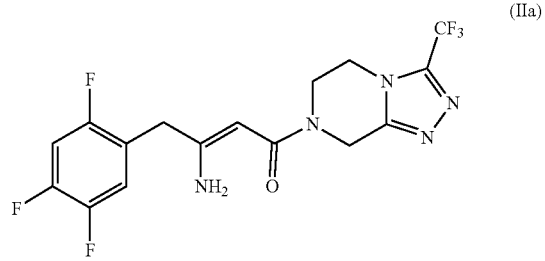 [SMILES: N/C(=C\C(=O)N1CCn2c(nnc2C(F)(F)F)C1)Cc1cc(F)c(F)cc1F]

(IIa)

and employing a rhodium catalyst on a bisphosphine ferrocenyl ligand selected from the group consisting of Ligand L3, Ligand L6, Ligand L7, and Ligand L8, wherein:

(a) Ligand L3 is 1,1'-Bis [2,5-dimethylphospholano] ferrocene:

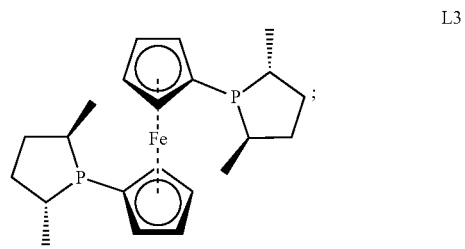

L3

(b) Ligand L6 is 1,1'-Bis [2,5-diethylphospholano] ferrocene:

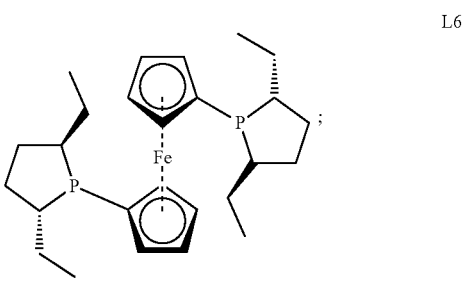

L6

(c) Ligand L7 is 1,1'-Bis (2,5-di-isopropylphospholano) ferrocene:

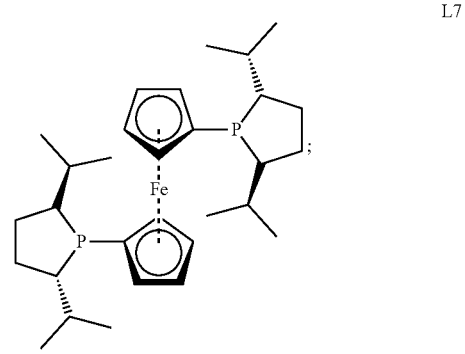

L7 and (d) Ligand L8 is 1,1'-Bis ((2,5)-2,5-di-ter-butylphospholano) ferrocene:

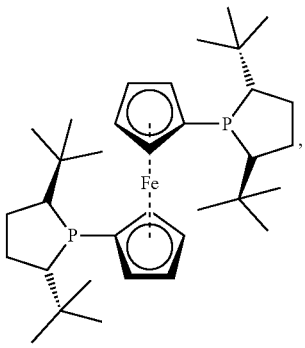

the process comprising:
(i) mixing the compound of Formula (IIa) with the rhodium catalyst, the bisphosphine ferrocenyl ligand, and an additive to obtain a first reaction mixture, wherein the additive is selected from the group consisting of salicylic acid, acetic acid, ammonium chloride, phosphoric acid, ammonium salicylate, butyl phosphoric acid, dibutyl phosphate, and tributyl phosphate;
(ii) adding a solvent in the first reaction mixture of (i) in an inert atmosphere of argon and stirring at a temperature of 25° C. for one hour to obtain a reaction slurry, wherein the solvent is methanol;
(iii) maintaining the reaction slurry obtained in (ii) under a hydrogen pressure of 10 bar to 30 bar at a temperature of 35° C. to 90° C. for 17 hours to 24 hours in an autoclave, followed by cooling at a temperature of 25° C. and releasing pressure to obtain a second reaction mixture; and
(iv) passing the second reaction mixture of (iii) through a neutral alumina bed followed by collecting a filtrate and drying a residue to afford the compound of Formula (Ia) with an enantiomeric excess of from 83% to 99.9%.

2. The process of claim 1, wherein the rhodium catalyst is [Rh(COD)$_2$OTf].

3. The process of claim 2, wherein the additive is selected from the group consisting of salicylic acid, acetic acid, phosphoric acid, ammonium salicylate, butyl phosphoric acid, dibutyl phosphate, and tributyl phosphate.

4. The process of claim 2, wherein the ligand is Ligand L6 or Ligand L7.

5. The process of claim 4, wherein the additive is selected from the group consisting of salicylic acid, acetic acid, phosphoric acid, ammonium salicylate, butyl phosphoric acid, and dibutyl phosphate.

6. The process of claim 2, wherein the ligand is Ligand L6 and the additive is selected from the group consisting of ammonium chloride, acetic acid, phosphoric acid, and salicylic acid.

7. The process of claim 2, wherein the ligand is Ligand L7 and the additive is selected from the group consisting of salicylic acid, acetic acid, ammonium chloride, phosphoric acid, ammonium salicylate, butyl phosphoric acid, and dibutyl phosphate.

* * * * *